United States Patent [19]

Charm

[11] 4,239,745
[45] Dec. 16, 1980

[54] ANTIBIOTIC DETECTION METHOD

[75] Inventor: Stanley E. Charm, Newton, Mass.

[73] Assignee: Penicillin Assays, Inc., Boston, Mass.

[21] Appl. No.: 963,146

[22] Filed: Nov. 22, 1978

Related U.S. Application Data

[63] Continuation-in-part of Ser. No. 853,541, Nov. 21, 1977, abandoned, Ser. No. 914,414, Jun. 12, 1978.

[51] Int. Cl.² .................. G01N 33/16; A61K 43/00; B65D 81/32
[52] U.S. Cl. .................................. 424/1; 23/230 B; 424/12; 422/61
[58] Field of Search .................. 424/1, 12; 23/230 B; 422/61

[56]  References Cited
    U.S. PATENT DOCUMENTS

| | | | |
|---|---|---|---|
| 3,673,410 | 6/1972 | Waite et al. | 424/1 |
| 3,817,837 | 6/1974 | Rubenstein et al. | 195/103.5 R |
| 3,852,157 | 12/1974 | Rubenstein et al. | 435/4 |

OTHER PUBLICATIONS

Edwards et al., Journal of Bacteriology, vol. 99, No. 2, 1969, pp. 459-462.
Blumberg et al., Bacteriological Reviews, vol. 38, No. 3, 1974, pp. 291-335.
Spratt, Evr. J. Biochem., vol. 72, 1977, pp. 341-352.

*Primary Examiner*—Benjamin R. Padgett
*Assistant Examiner*—Christine M. Nucker
*Attorney, Agent, or Firm*—Kenway & Jenney

[57]  ABSTRACT

A process for rapidly detecting as little as 0.001 I.U./ml of antibiotic in a sample of liquid such as milk. The process comprises the steps of incubating the sample together with a tagged antibiotic or antibiotic precursor and antibiotic sensitive cells under conditions which allow antibiotic molecules to attach to receptor sites in or on the cells, separating the cells with immobilized antibiotic from the remainder of the reaction mixture, and determining the quantity of tagged antibiotic on the cells. The amount of tagged antibiotic on the cells is a function of the quantity of antibiotic present in the sample.

24 Claims, 2 Drawing Figures

ANTIBIOTIC DETECTION METHOD

REFERENCE TO RELATED APPLICATIONS

This application is a continuation-in-part of copending applications Ser. No. 853,541 filed Nov. 21, 1977, entitled "Antibiotic Detection Method", (now abandoned) and Ser. No. 914,414 filed June 12, 1978 entitled "Improved Antibiotic Detection Method".

BACKGROUND OF THE INVENTION

This invention relates to a rapid, sensitive method for detecting the presence of antibiotics in liquids such as milk, body fluids, meat extracts, and fermentation broths.

The ability to detect small concentrations of antibiotics in liquids is important in various situations. One example is the food industry where the use of antibiotics in the treatment of animals which produce food stuffs has created a need for a rapid, accurate test method which can be used in the field by bulk food handlers and the like. Because penicillins are used to treat mastitis in dairy cattle, and because the Food and Drug Administration restricts the penicillin content of milk, antibiotic detection methods suitable for rapidly and accurately screening milk are particularly important. Thus, the growing medical concern about ingestion of small amounts of antibiotics by humans is directing attention to the incidence of penicillin in milk at levels in the range of 0.010–0.050 I.U./ml or greater and to simple screening methods for detecting such minute quantities of penicillin and other antibiotics.

At the present time, there are a variety of known antibiotic detection procedures. Most of these involve microbiological techniques wherein the presence or absence of penicillin or other antibiotic is determined by observing the inhibition of growth of antibiotic sensitive microorganisms in the presence of the test sample. Formerly, such procedures required incubation times of four hours or more, but by employing microorganism strains "supersensitive" to antibiotics, the time required to perform the assays has been reduced to between 2 and 2½ hours.

Other antibiotic detection techniques exploit various other unique properties of the antibiotic or class of antibiotics to be detected as a test basis. Thus, in *Immobilized Enzyme-Based Flowing-Stream Analyzer for Measurement of Penicillin in Fermentation Broths*, J. F. Rusling et al., Analytical Chemistry, Vol. 48, p. 1211, (July, 1976), a test based on the enzymatic hydrolysis of penicillin with an immobilized $\beta$ lactamase derivative is disclosed. *Simple Ultrasensitive Test for Detecting Penicillin in Milk*, J. M. A. Palmer et al., J. Dairy Science, Vol. 50, p. 1390, discloses a penicillin detection method based on the growth of *Bacillus subtilis* spores on nutrient-spore-dye paper discs residing in a small sample of milk exposed to the air. As the water content of the milk evaporates, penicillin concentration, if any, increases and induces a color change in the dye which is indicative of concentration. U.S. Pat. No. 3,586,483 to J. G. Heider et al. discloses a method of detecting tetracycline antibiotics in fluids by absorbing the fluid on an absorbent strip containing a complexing metal which forms a fluorescent metal complex with the antibiotic, and by observing the fluorescence of the metal complex under ultraviolet light.

The foregoing and other available detection techniques vary widely with respect to their sensitivity and speed. It is believed that no presently available test is capable of detecting as little as 0.01 I.U. of penicillin per milliliter (6 ng/ml) in less than an hour. If such a test were available, it would become economical to rapidly and reliably determine, for example, whether milk sampled in the field from relatively small batches contained antibiotic concentrations in excess of Food and Drug Administration standards.

SUMMARY OF THE INVENTION

The instant invention provides a novel procedure for detecting the presence of antibiotics in liquids. Certain embodiments of the invention are ideally suited for screening milk for penicillin type antibiotics, and the invention will be described in detail with reference to this application. However, in view of the description which follows, it will be apparent that the invention may be used to assay body fluids, meat extracts, fermentation broths and the like for a variety of antibiotic drugs. The outstanding advantage of the process of the invention is that it is capable of detecting very small antibiotic concentrations, e.g., 0.001 I.U./ml of penicillin, and can do so rapidly, e.g., in less than about 10 minutes.

In its broadest aspects, the process of the invention comprises the steps of incubating the sample with cells, or in some cases, cellular subunits, of an antibiotic sensitive microorganism under conditions to allow antibiotic molecules that may be present in the sample to attach to receptor sites associated with the cells, incubating the cell-sample mixture with a tagged antibiotic or antibiotic precursor under the same conditions, separating the cells from the liquid portion of the reaction mixture, determining the amount of tagged antibiotic present either in association with the separated cells or the remaining liquid, and comparing the determination to a standard. if antibiotic molecules were present in the sample, then the tagged and untagged molecules both seek to attach themselves onto a finite number of receptor sites on the cells or cellular subunits, and the amount of tagged antibiotic which becomes immobilized is inversely proportional to the concentration of antibiotic in the test sample. Similarly, the amount of tagged antibiotic which remains in the liquid phase will be a function of original antibiotic concentration.

The surprising sensitivity and speed of the test is believed to be a consequence of both the high binding constant characteristic of the attraction between antibiotic molecules and receptor sites on cell walls or other subcellular structures of antibiotic sensitive organisms, and the specificity of antibiotic molecules for their sites of action on such organisms. For example, the binding constant for penicillins with receptor sites on gram positive cells is orders of magnitude greater than the binding constant for the antigen-antibody immunochemical reaction on which analogous detection techniques (immunoassays) have been based.

In an important embodiment of the process of the invention, in the interest of providing a rapid test suitable for use in screening milk, a single incubation is conducted involving the antibiotic sensitive microorganism, the sample to be tested, and the tagged antibiotic or antibiotic precursor, and the separation step is effected by centrifugation. Both the speed and sensitivity of the assay are promoted by employing cell strains which are supersensitive to a class of antibiotics or specific antibiotic to be detected. Extending this concept one step further, the preferred antibiotic sensitive microorganisms are strains having a temperature of optimum growth above about 50° C. In this situation, the incubation can be conducted at relatively high temperatures and the kinetics of the antibiotic-receptor site organic reaction are enhanced. The preferred microorganism for conducting assays for β lactam antibiotics is *Bacillus stearothermophilus* (A.T.C.C. No. 10149 or 15952). However, various other antibiotic supersensitive cell strains can be used, and indeed, merely sensitive strains can be used if reduced sensitivity can be tolerated. Nonlimiting examples of suitable cell strains include certain mutants of *E. coli, Ps. aeruginosa, B. subtilis*, and *S. aureus*.

In embodiments of the process of the invention wherein speed is less important than sensitivity, the sample and cell culture are incubated for a time and the tagged antibiotic is added later. When employing sensitive microorganisms having the high optimum growth rate, it has been noted that sensitivity does not increase linearly with time and that incubations of greater than 15 minutes in duration should not be conducted.

In preferred embodiments of the invention, the tagged antibiotic is benzylpenicillin, or the antibiotic precursor 6 amino penicillanic acid, and the antibiotic to be detected is a β lactam antibiotic such as benzylpenicillin, cephalosporin, ampicillin, oxacillin, methicillin, cloxacillin, cephaloridine, and cephalothin. Other nonlimiting antibiotics which can be detected include erythromycin, lincomycin, actinomysin, vancomycin, bacitracin and aminoglycosides such as streptomycin, gentamycin, kanamycin, and neomycin. The process of the invention works exceptionally well with penicillin or penicillin-like antibiotics of the type which inhibit cell reproduction by attaching to sites on cell membranes to inhibit cell wall synthesis. However, antibiotics having other sites of action such as rifamycin and tetracyclines can also be detected. The tagged antibiotic can be tagged with a radioactive atom, an enzyme, enzyme inhibitor, or a coenzyme. The presently preferred tag is a $^{14}C$ included in the structure of the antibiotic molecule or an $^{125}I$ atom attached to the antibiotic via reaction with, for example, tyrosine or a suitable derivative thereof.

In accordance with another aspect of the invention, a test set for determining the presence of antibiotics in liquid samples is provided. The set has a quantity of concentration stabilized antibiotic sensitive (preferably supersensitive) cells, a quantity of tagged antibiotic or antibiotic precursor selected to have a high binding constant with the sites on the cells, and a standard against which the results of tests made with the reagents can be compared. In preferred embodiments, the test set includes freeze dried *Bacillus stearothermophilus*, the tagged antibiotic is benzylpenicillin tagged with a radioactive atom, e.g., $^{14}C$, and the standard is either a standard curve or at least one sample containing a known concentration of the antibiotic or class of antibiotics to be detected.

Accordingly, objects of the invention include the provision of an antibiotic detection technique which is capable of detecting a large number of different antibiotic drugs in a variety of liquid media, which can be adapted to be very rapid and acceptably sensitive, and which can be adapted to be slightly slower, but extraordinarily sensitive. Another object of the invention is to provide a fast antibiotic detection technique which can be conveniently conducted outside of the laboratory.

Another object is to provide a test set suitable for determining the presence of as little as 1 ng/ml of antibiotic in a liquid sampled from materials such as milk, body fluids, meat residues, fermentation broths and the like.

These and other objects and features of the invention will be apparent from the following detailed description of some important embodiments.

DESCRIPTION OF THE PREFERRED EMBODIMENT

Figure 1:
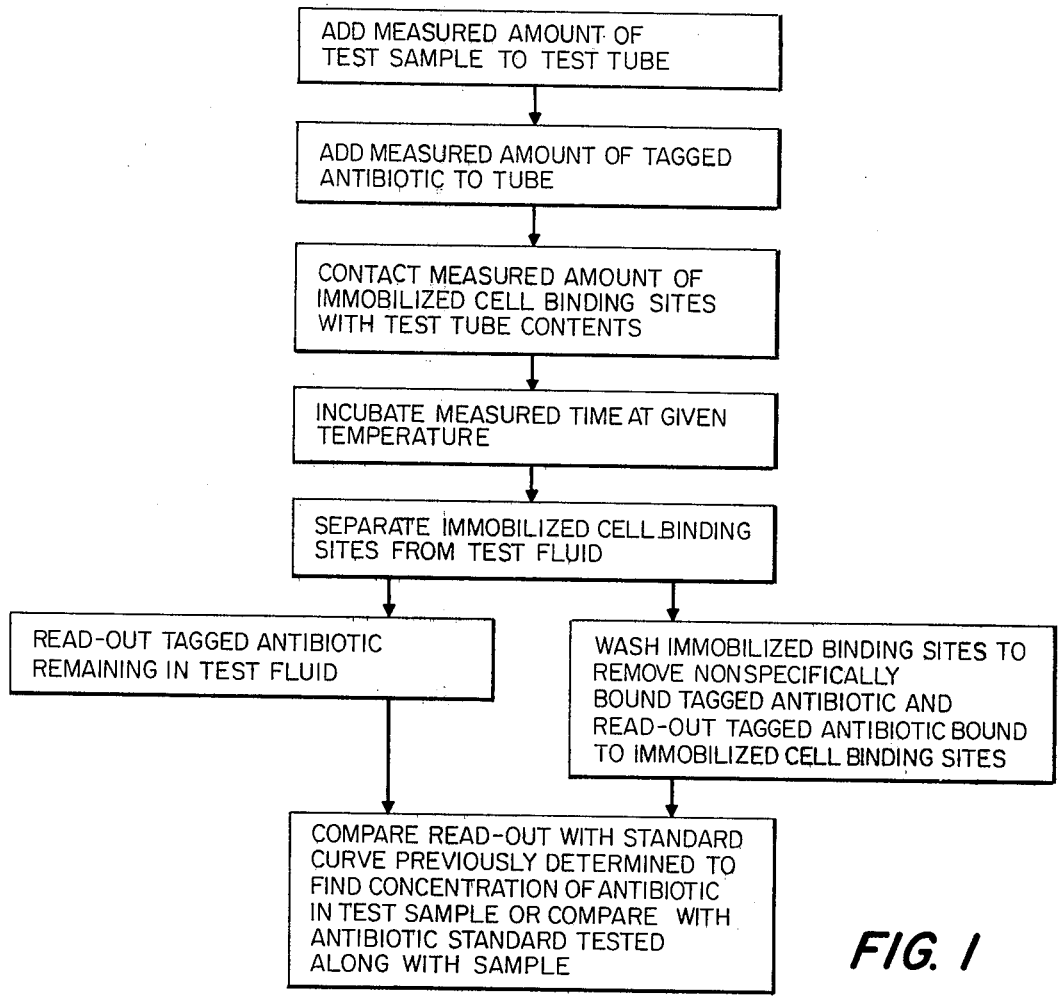
FIG. 1 is a flow chart illustrating the antibiotic detection process of the invention.

The process of the instant invention involves four basic steps: an incubation wherein antibiotic (if any) in the sample and tagged antibiotic become bound to antibiotic sensitive cells or cell subunits; a separation wherein the cells with bound antibiotic are isolated from the remainder of the system; a determination wherein an indication of the quantity of tagged antibiotic associated either with the cells or the separated liquid is obtained; and a comparison wherein the determination is compared with a standard. As the concentration of antibiotic in the test sample increases, fewer tagged antibiotic molecules will report in association with the cells (and more with the separated liquid).

By preparing a series of samples of known antibiotic concentration and treating them in accordance with the process of the invention, a standard curve of antibiotic concentration versus counts per minute (in case of radioactive tags) or the like can be produced. Assays of unknowns will give a quantitative indication of the antibiotic concentration if compared with such a curve. An indication of the presence of antibiotic in a sample may also be obtained by comparing the test sample read out of tagged antibiotic with the results of assays run in parallel with samples containing known amounts of antibiotic. If only the presence of antibiotic in concentrations above a certain maximum is sought, the necessary comparison step may be conducted indirectly. This is done by noting the read out associated with the test sample and comparing with a previously determined read out which has been correlated with the critical antibiotic concentration. This simple comparison is made possible by the standardization of reagents and procedure. Thus, the technician conducting the test inherently makes the comparison when he interprets the read out.

It is believed that the favorable sensitivity and speed characteristic of the assay are traceable to the typically high binding constants for the reactions between antibiotics and cells and to the specificity of the antibiotics for their sites of action. Thus, in the process of the invention, even extremely small quantities of antibiotic in a test sample rapidly become attached to receptor sites on the cell membrane or other location on the microorganism with which it is incubated. In this regard, it is well known that many antibiotics operate by attaching themselves onto certain cell locations, thereby preventing normal reproductive metabolism. For example, vancomycin, bacitracin, penicillins, and cephalosporins are known to inhibit cell reproduction by attaching to receptor sites on the cell membranes to thereby prevent cell wall synthesis. See, for example, *Correlation between Growth Inhibition and the Binding of Various Penicillins and Cephalosporins to Staphylococcus aureus*, J. R. Edwards et al., Journal of Bacteriology, August 1969, p. 459-462; and *The Actions of Penicillin and Other Antibiotics on Bacterial Cell Wall Synthesis,* J. L. Strominger, Hopkins Med. J., V. 133, p. 63 (1973). Other antibiotics have sites of action somewhat less accessible than the cell membrane, but nevertheless operate by attaching themselves to specific cell locations such as ribosomes or nucleic acids. Accordingly, in addition to the β lactam antibiotics and other antibiotics set forth above, the process of the invention can detect erythromycin, lincomycin, actinomycin, and tetracyclines, as well as aminoglycosides such as streptomycin, neomycin, etc. These latter substances have various sites of action associated with the cells such as ribosomes and the like.

If tagged antibiotics are included in the incubation with the sample, then tagged and untagged molecules compete for the available receptor sites. If the tagged molecules are added after the sample has been incubated with the cells for a time, then tagged antibiotic molecules attach to remaining receptor sites. In either case, since by detecting the presence of tagged molecules immobilized on the cells one can obtain a measure of the extent of tagged antibiotic binding, an indirect measure of untagged molecule binding results since the amount of tagged antibiotic on the cells is a function of the quantity of antibiotic present in the sample.

Stated differently, the process of the invention depends on tagged antibiotic molecules and antibiotic which may be present in the sample seeking to react with a finite number of receptor sites on the cells either simultaneously or sequentially. Thus, a successful test may be conducted where the antibiotic to be detected and the tagged substance are the same antibiotic. However, any suitably tagged member of the class of antibiotics or related molecules such as antibiotic precursors or derivatives which attaches to the same group of receptor sites as the antibiotic to be detected can be used in the incubation. For example, any specific penicillin or cephalosporin antibiotic, suitably tagged, can be used to detect the same, any other, or a mixture of penicillins or cephalosporins. However, preferred antibiotics used for tagging are those members of a given class which have a high binding constant such as benzylpenicillin (penicillin G), ampicillin, or cephalosporidine in the class of β lactam antibiotics. An example of an antibiotic precursor in this class is 6 amino penicillanic acid; an example of a derivative is the reaction product of 6 aminopenicillanic acid and tyrosine. As used below, the term "tagged antibiotic" includes tagged antibiotic precursors and derivatives which have an affinity for the sites of action of their parent antibiotic.

Regarding the nature of the tag, the state of the art is such that there are several types of tags available. Thus, the tagged antibiotic can contain a $^{14}C$, or $^{125}I$, or other radioactive atom detectable by a counter or the like, or an enzyme, enzyme inhibitor, (e.g. methotrexate) or coenzyme (e.g. NAD) which are detectable by subjecting the tagged antibiotic to a substrate solution which undergoes a reaction under the catalytic influence of the tag, or in which a reaction is inhibited. Excellent results have been obtained using radioactively tagged antibiotics, many of which, for example, $^{14}C$ tagged benzylpenicillin (penicillin G), are now commercially available. Those skilled in the art will appreciate that in most cases a derivative of the antibiotic molecule must be synthesized in order to furnish a site of attachment for a radioactive iodine atom. Enzymes and coenzymes such as dehydrogenase coenzymes can also be employed as a tag. The quantitative determination of the coenzyme would be accomplished by subjecting the separated cells (or remaining liquid) to a solution containing a substrate which changes color when acted upon by an enzyme system, a critical component of which is the coenzyme. The other enzymes in the system are included in the solution.

Broadly, the cells which can be used in the process of the invention comprise any cell which is sensitive to the antibiotic to be detected. Thus, for example, any microorganism that is inhibited by penicillin could be used to detect penicillin type antibiotics. However, to improve sensitivity, it is much preferred to employ a microorganism which is "supersensitive" to the antibiotic to be detected. In recent years, many strains of cells supersensitive to either specific antibiotics or classes of antibiotics have become available. Examples of β lactam sensitive microorganisms include *B. subtilis, B. megaterium, S. aureus, Ps. aeruginosa,* and certain mutants of *E. coli.* Most favorable results in terms of speed and sensitivity have been achieved using supersensitive microorganism strains which have an optimum temperature of growth generally in excess of about 50° C. The preferred microorganism in this regard is *Bacillus stearothermophilus* (A.T.C.C. No. 10149). *B. stearothermophilus* A.T.C.C. No. 15952 may also be used. Because the incubations can be conducted at high temperature with this type of microorganism, the rate of antibiotic binding is increased.

It should also be noted that whole cells need not necessarily be used in the process of the invention. Thus, the cellular subunits on which the receptor sites are located, e.g., cell walls or membranes, ribosomes, enzymes, etc., may be used in place of the intact cells. For example, penicillin G is known to bind to and inhibit the action of D-alanine carboxypeptidase which is normally immobilized on cell membranes. However, methods are now available for the isolation of such materials, and these may be used in place of whole cells (see, *Purification and Characterization of Thermophilic D-Alanine Carboxypeptidase from Membranes of B. stearothermophilus,* R. Rogers et al., J. Biol. Chem. V. 249 p. 4863-4876). While separation of such subunits from the remainder of the reaction mixture may be difficult to accomplish quickly unless the subunits are immobilized on an insoluble solid or the like, those skilled in the art will appreciate that the use of such materials will be the equivalent of using whole cells.

The process of the invention can also be practiced using cells immobilized on a suitable support such as a collagen matrix, polyacrylamide gel, or a small quantity of a shape retaining nutrient agar attached to a dip stick. In this situation, separation of the cells from the liquid components of the reaction mixture is greatly simplified and speeded up. When whole cells are used, the preferred method of separation is by centrifugation. However, other methods of separating the cells from the remainder of the reaction mixture, e.g., ultrafiltration, can be employed.

In view of the foregoing it will be appreciated that the test of the invention may be adapted to detect the presence of a variety of antibiotics or mixtures thereof in a number of different liquid media. A variety of tagged antibiotics and cells or cell subunits may be used, and either a qualitative or quantitative test may be designed. The invention will now be described with reference to a specific, nonlimiting embodiment suitable for rapidly screening milk samples for the presence of as little as 0.001 I.U./ml of penicillin.

EXAMPLE I

*Bacillus stearothermophilus* was grown in accordance with the following.

Medium:

| Solution A | Difco yeast extract | 2.58 kg |
| --- | --- | --- |
|  | Difco bactotryptone | 2.58 kg |
|  | Sodium phosphate, dibasic | 1.54 kg |
|  | Potassium phosphate, monobasic | 515 g |
|  | Ammonium sulfate | 515 g |
|  | Distilled water | 515 liters |
| Solution B | Magnesium sulfate, anhydrous | 103 g |
|  | Distilled water | 1.29 liters |
| Solution C | Calcium chloride . 2 H$_2$O | 12.9 g |
|  | Manganese chloride | 0.52 g |
|  | Distilled water | 1.29 liters |
| Solution D | Glucose | 2.58 kg |
|  | Distilled water | 12.9 liters |

Conditions: 60° C., aeration, 10% inoculum
Growing time: 2.5 hours

Procedure:

Solution A is sterilized in the fermentor. Solution B is sterilized separately and 2.5 ml added to each liter of Solution A. The final concentration of magnesium sulfate in the medium is 0.2 g/liter. Solution C is sterilized separately and 2.5 ml added to each liter of Solution A. The final concentration in the medium is:

| calcium chloride . 2 H$_2$O | 0.025 g/liter |
| --- | --- |
| manganese chloride | 0.001 g/liter |

Solution D is sterilized separately and 25 ml added to each liter of Solution A. The final concentration of glucose in the medium is 5 g/liter.

The temperature of Solution A in the fermentor should be between 60°–65° C. Solutions B, C, and D are added with vigorous stirring of the fermentor. Slow addition of Solution C and vigorous stirring were necessary to prevent the formation of a precipitate. The complete medium has a pH of 6.9 without adjustment. Dow Corning B antifoam is added to give a concentration of 0.1%. Very vigorous aeration is required for growth of the organism.

When the fermentation is initiated, a carboy containing six liters of complete medium is inoculated with the contents of two one-liter Ehrlenmeyer flasks, each of which contains 150 ml of a culture grown overnight. When a reading of O.D. 0.150 (600 mu) is attained, the entire contents of the carboy are used to inoculate the 60 liter fermentor. When the solids are 0.03%, the 60 liter fermentor is used to inoculate the 530 liter fermentor.

The cells are washed twice with five volumes of 0.2 M NH$_4$Cl, pH 7.0, then twice with 10 volumes of a buffer containing 0.01 M magnesium acetate, 0.01 M mercaptoethanol, and 0.02 M Tris-HCl buffer, pH 7.8.

The cells were then centrifuged and after decanting the supernatant, were resuspended in a mixed solution of A, B, and C (above) and dispensed into vials. The contents of each vial can be freeze dried by known methods and stored at about 4° C. for extended periods of time. Freeze drying in the growth medium (minus glucose solution) preserves the maximum antibiotic binding activity of the cells. Such freeze dried cells constitute an ideal concentration stabilized source of cells for use in a test set.

The tagged antibiotic employed was benzylpenicillin containing a $^{14}$C atom (150 μcurie/mg) and was purchased from Amersham Searle Co. This reagent can also be freeze dried for stability.

To obtain quantitative results and to act as a control, two or more liquid samples, one of which is known to be antibiotic free and the other of which contains a known quantity of the antibiotic to be detected, e.g., 0.01 unit per ml of penicillin, can be tested in parallel. These samples can also be freeze dried for stability. Any of the foregoing reagents can be reconstituted with distilled water or phosphate buffer having a slightly acidic pH. For penicillins, binding occurs optimally between pH 6.0–7.0. The stabilized cells, tagged antibiotic, and controls (or standard curve) constitute a test set suitable for conducting assays in accordance with the invention.

The reagents set forth above were used to prepare a standard curve and to test unknowns for the presence of penicillin. One standard curve was prepared by subjecting 12 1.0 ml milk samples containing known concentrations of benzylpenicillin (penicillin G) to an incubation with a (1) 100 ml sample of a *B. stearothermophilus* suspension (reconstituted from freeze dried material by adding 2.5 ml distilled water to a vial produced as set forth above) and (2) $^{14}$C tagged benzylpenicillin (penicillin G) in sufficient quantity to give about 10,000 counts/minute. The incubation was conducted for three minutes in a dry bath incubator set at 90° C. The cells were then separated by centrifugation at 3,000 xg for two minutes. The supernatant was discarded, and the tube was rinsed with phosphate buffer without disturbing the cells. The cells were then transferred from the tube to a scintillation vial using scintillation fluid as a wash. This latter step may be eliminated and the tagged molecules directly detected if a $^{125}$I tag is used. Results are set forth in table I below:

TABLE I

Standard Curve for Detection of Benzylpenicillin

| Sample No. | [Benzylpen] ng/ml | Counts/ 10 min. | Background Corrected Counts/10 min. | Average Counts/10 min. | C/C$_o$** |
| --- | --- | --- | --- | --- | --- |
| 1 | * | 331 | 84 |  |  |
|  |  |  |  | 102 | .007 |
| 2 | * | 367 | 120 |  |  |
| 3 | 0 | 15457 | 15210 |  |  |
|  |  |  |  | 15272.5 | 1.000 |
| 4 | 0 | 15582 | 15335 |  |  |
| 5 | 1.0 | 13165 | 12918 |  |  |
|  |  |  |  | 13019.5 | .853 |
| 6 | 1.0 | 13368 | 13121 |  |  |
| 7 | 5.0 | 9859 | 9612 |  |  |
|  |  |  |  | 10002. | .655 |
| 8 | 5.0 | 10639 | 10392 |  |  |
| 9 | 10 | 7615 | 7368 |  |  |
|  |  |  |  | 7699 | .504 |
| 10 | 10 | 8277 | 8030 |  |  |
| 11 | 50 | 4175 | 3920 |  |  |
|  |  |  |  | 4071 | .267 |
| 12 | 50 | 4461 | 4214 |  |  |

*20,000 units benzylpenicillin (penicillin G) added to sample.
**Counts of sample/counts of control (zero penicillin G present in sample).

Figure 2:
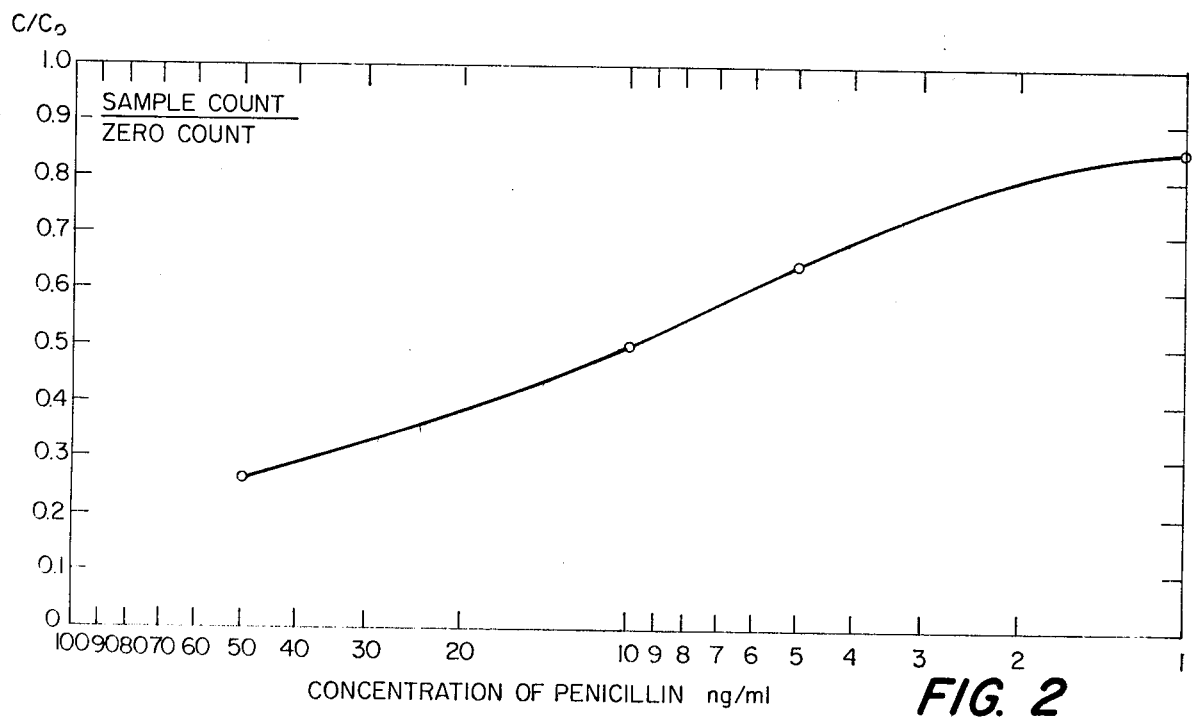
FIG. 2 is a standard curve for benzylpenicillin.

As can be appreciated from the foregoing table, a significant and dramatic decrease in the count occurs as the amount of benzylpenicillin in the samples is increased from zero (3,4) to 10 ng/ml (9, 10). The data in Table I is graphically presented in FIG. 2, wherein penicillin concentration in ng/ml is plotted vs. sample count/zero count.

Using the foregoing table as a standard of comparison, tests were conducted on 20 milk samples prepared by a commercial milk processor. The procedure employed was identical to the procedure for preparing the standard curve set forth above except for the additional step of comparing the counts/minute obtained with the test samples with the curve and converting ng/ml of penicillin to I.U./ml. (0.01 I.U./ml≈6 ng). The results of these tests are set forth in table II below:

TABLE II

Comparison of Sensitivity of Microbiological Technique and Technique of the Invention

| Sample No. | Known Penicillin Concentration IU/ml | Assay Results Using Microbiological Technique (IU/ml) | Test Results (per ml) IU |
|---|---|---|---|
| 1 | .005 | — | .007 |
| 2 | .005 | — | .009 |
| 3 | .003 | — | .008 |
| 4 | .002 | — | .003 |
| 5 | .000 | — | .002 |
| 6 | .007 | — | .006 |
| 7 | .000 | — | .001 |
| 8 | .042 | .1 | .005 |
| 9 | .003 | — | .004 |
| 10 | .030 | .06 | .07 |
| 11 | .020 | .04 | .05 |
| 12 | .020 | .03 | .04 |
| 13 | .025 | .02 | .03 |
| 14 | .037 | .05 | .06 |
| 15 | .007 | — | .01 |
| 16 | .017 | .01 | .02 |
| 17 | .043 | .09 | .10 |
| 18 | .022 | .08 | .09 |
| 19 | .030 | .07 | .08 |
| 20 | .000 | — | <.001 |

It should be noted that the foregoing tests consistently detected the presence of as little as 0.01 I.U./ml of penicillin in about 6 minutes of testing time (not including counting time).

It should also be noted that the foregoing procedure involved the simultaneous incubation of both the sample and tagged penicillin for only three minutes and a two minute centrifugation. This test was specifically designed to be acceptably sensitive and as rapid as possible.

Another group of tests were run to demonstrate the sensitivity possible using *B. stearothermophilus*, tagged benzylpenicillin (1500 CPM), and the three minute incubation in a dry bath incubator set at 90° C. The results of this series of tests are set forth in Table III below. The data set forth in table III illustrate that a significant depression in the counts/minute associated with the separated cell fraction occurs when the antibiotic concentration of the sample is raised from zero up through 0.001 I.U./ml, 0.002 I.U./ml and 0.005 I.U./ml. This test may be conducted, including the counting step, in less than 10 minutes.

TABLE III

| Sample No. | I.U. Pen. G present in sample | Counts/Min. of cells | Average Counts/Min. |
|---|---|---|---|
| 1 | 0 | 365 | |
| | | | 338 |
| 2 | 0 | 311 | |
| 3 | .001 | 207 | |
| | | | 217 |
| 4 | .001 | 227 | |
| 5 | .002 | 191 | |
| | | | 183.5 |

TABLE III-continued

| Sample No. | I.U. Pen. G present in sample | Counts/Min. of cells | Average Counts/Min. |
|---|---|---|---|
| 6 | .002 | 176 | |
| 7 | .005 | 97 | |
| | | | 100 |
| 8 | .005 | 103 | |
| 9 | .010 | 89 | |
| | | | 100.5 |
| 10 | .010 | 112 | |
| 11 | — | 27 | |

EXAMPLE II

Another group of tests was run to demonstrate the speed and sensitivity with which streptomycin can be detected. Six five-milliliter samples of milk were mixed with streptomycin to result in samples containing 0 ng/ml, 1 ng/ml, 10 ng/ml, 100 ng/ml, 1000 ng/ml, and $10^6$ ng/ml. Each sample was mixed with tritium-labelled dihydrostreptomycin of 228,000 counts/minute (commercially available for example from Amersham Searle Co.) and with *B. stearothermophilus* suspension prepared as described above for Example I and reconstituted from 0.2 ml freeze dried material diluted with 8 ml water. (One suitable concentration of the material prior to freeze drying is attained by resuspending the centrifugally-separated cells, as described in Example I, to a concentration such that a 1 to 500 dilution has an optical density (O.D.) of 0.60 at a wavelength of 600 millimicrons.) The mixtures were heated to facilitate the binding of the tritium-labelled dihydrostreptomycin at its binding site in the cells. In this example, accordingly, samples initially at 10°–20° C. were heated at 90° C. in a dry block heater for three minutes so that the temperature of the samples reached 60°–65° C. The samples were then centrifuged for three minutes at $3,000 \times g$, the supernatants decanted, and each precipitate washed twice with distilled water. The precipitates (cells) were then transferred, with scintillation fluid, to scintillation vials, and the counts read for one minute. The results of these tests are in Table IV set forth below.

TABLE IV

| Sample No. | Streptomycin Concentration (per ml) | Count (cpm) | Count/ Control Count (%) |
|---|---|---|---|
| 1 | 0 | 30,441 | 100 |
| 2 | 1 ng | 25,849 | 84.9 |
| 3 | 10 ng | 22,644 | 74.5 |
| 4 | 100 ng | 18,123 | 59.6 |
| 5 | 1000 ng | 14,819 | 48.7 |
| 6 | $10^6$ ng | 8,707 | 28.6 |

As can be appreciated from the foregoing table, a significant decrease in the count occurs as the amount of streptomycin in the sample is increased from zero (sample 1) through one, ten and 100 ng/ml, and greater. Accordingly, the presence of streptomycin in samples containing as little as 1 ng/ml can be detected by treating the sample in accordance with the foregoing procedure, and comparing the count with the data in the table. Such determinations may be conducted in about eight minutes.

In view of the foregoing discussion, those skilled in the art will appreciate that it is possible to detect even smaller concentrations of antibiotics by, for example, incubating the sample with the antibiotic sensitive cells for sufficient time to enable all antibiotic present in the sample to attach to receptor sites. The tagged antibiotic would be added thereafter and would attach to any remaining receptor sites. Aside from these modifications, the procedure would be substantially identical to that set forth above and would result in a slightly slower but even more sensitive test.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A process for detecting the presence of an antibiotic in a liquid sample, said process comprising the steps of:
   A. incubating the sample with cells of a microorganism, said microorganism being sensitive to said antibiotic and having receptor sites capable of binding to said antibiotic, said incubation being conducted under conditions to allow antibiotic molecules, if present in the sample, to bind to said receptor sites;
   B. incubating the mixture of step A with a tagged antibiotic capable of binding with said receptor sites;
   C. separating the cells from the liquid;
   D. determining the amount of tagged antibiotic associated either with the separated cells or with the liquid; and
   E. comparing the determination of step D with a standard to obtain an indication of the presence of antibiotic in the sample.

2. The process as set forth in claim 1 wherein the amount of tagged antibiotic associated with the cells is determined.

3. The process as set forth in claim 1 wherein steps A and B are conducted simultaneously.

4. The process as set forth in claim 1 wherein the tag on said tagged antibiotic is a radioactive atom.

5. The process as set forth in claim 1 wherein the antibiotic to be detected is a $\beta$ lactam antibiotic, the tagged antibiotic includes a $\beta$ lactam moiety, and the microorganism is a $\beta$ lactam antibiotic sensitive microorganism.

6. The process as set forth in claim 5 wherein the microorganism is Bacillus stearothermophilus.

7. The process as set forth in claim 1 wherein the antibiotic sensitive microorganism is supersensitive to the antibiotic to be detected.

8. The process as set forth in claim 1 wherein the antibiotic sensitive microorganism is a strain having a temperature of optimum growth above 50° C.

9. The process as set forth in claim 1 wherein the separation step is effected by centrifugation.

10. The process as set forth in claim 1 wherein the liquid sample is selected from the group consisting of milk, body fluids, liquids extracted from meat, and fermentation broths.

11. The process as set forth in claim 1 wherein the antibiotic to be detected and the tagged antibiotic are the same.

12. The process as set forth in claim 1 wherein the antibiotic to be detected is selected from the group consisting of benzylpenicillin, cephalosporin, ampicillin, oxacillin, methicillin, cloxacillin, cephalosporidine, and cephalothin, and the tagged antibiotic is a $^{14}C$ tagged substance selected from the group consisting of 6 amino penicillanic acid and benzylpenicillin.

13. The process as set forth in claim 1 wherein the antibiotic to be detected is streptomycin.

14. A process capable of detecting the presence of at least 0.01 I.U. of $\beta$ lactam antibiotic in a milk sample in less than 10 minutes, said process comprising the steps of:
   A. incubating the sample and a tagged $\beta$ lactam antibiotic with cells of a $\beta$ lactam antibiotic supersensitive microorganism so that tagged molecules and antibiotic molecules that may be present in the sample compete for attachment to receptor sites on the cells;
   B. centrifuging the mixture of step A to separate the cells from the remainder of the reaction mixture;
   C. washing the separated cells;
   D. determining the amount of tagged antibiotic or antibiotic precursor present on the cells; and
   E. comparing the determination of step D with a standard to obtain an indication of the presence of antibiotic in the sample.

15. The process as set forth in claim 14 wherein the tagged antibiotic is benzylpenicillin having a radioactive atom bound thereto.

16. The process as set forth in claim 14 wherein the tagged antibiotic is selected from the group consisting of $\beta$ lactam antibiotic precursors and $\beta$ lactam antibiotic derivatives.

17. The process as set forth in claim 14 wherein the antibiotic supersensitive microorganism is a microorganism having an optimum temperature of growth above about 50° C. and the temperature of the incubation is above 50° C.

18. The process as set forth in claim 17 wherein the microorganism is B. stearothermophilus.

19. A test set for detecting the presence of antibiotic in a liquid sample, said set comprising:
   A. a contained quantity of concentration stabilized cells supersensitive to said antibiotic;
   B. a contained quantity of a tagged antibiotic having a high binding rate with said cells when incubated therewith; and
   C. a standard to which the results of tests made with said cells and said tagged antibiotic may be compared.

20. The test set as set forth in claim 19 wherein the cells comprise freeze dried B. stearothermophilus and the tagged antibiotic is benzylpenicillin tagged with radioactive atom.

21. The test set as set forth in claim 19 wherein the tag is selected from the group consisting of $^{125}I$, and $^{14}C$.

22. The test set as set forth in claim 19 wherein said standard comprises a standard curve.

23. The test set as set forth in claim 19 wherein said standard comprises at least one sample containing a known concentration of the antibiotic to be detected.

24. The test set as set forth in claim 19 wherein the tagged antibiotic is tritium labelled tetrahydrostreptomycin.

* * * * *